(12) United States Patent
Trombley, III et al.

(10) Patent No.: US 6,620,134 B1
(45) Date of Patent: Sep. 16, 2003

(54) SYRINGES AND INJECTOR SYSTEMS WITH COLLAPSIBLE CARTRIDGES

(75) Inventors: Frederick W. Trombley, III, Gibsonia, PA (US); Arthur E. Uber, III, Pittsburgh, PA (US)

(73) Assignee: Medrad, Inc., Indianola, PA (US)

( * ) Notice: Subject to any disclaimer, the term of this patent is extended or adjusted under 35 U.S.C. 154(b) by 0 days.

(21) Appl. No.: 09/831,125

(22) PCT Filed: Nov. 19, 1999

(86) PCT No.: PCT/US99/27574

§ 371 (c)(1),
(2), (4) Date: May 4, 2001

(87) PCT Pub. No.: WO00/30703

PCT Pub. Date: Jun. 2, 2000

Related U.S. Application Data

(60) Provisional application No. 60/109,476, filed on Nov. 23, 1998.

(51) Int. Cl.[7] .............................................. A61M 37/00
(52) U.S. Cl. ...................................... 604/133; 604/212
(58) Field of Search ................................ 604/131, 133, 604/151–154, 212–216, 232

(56) References Cited

U.S. PATENT DOCUMENTS

| 3,527,215 A | * | 9/1970 | DeWitt ........................ 604/214 |
|---|---|---|---|
| 4,006,736 A | | 2/1977 | Kranys et al. |
| 4,677,980 A | | 7/1987 | Reilly et al. |
| 4,758,226 A | * | 7/1988 | Carre .......................... 222/14 |
| 5,000,739 A | * | 3/1991 | Kulisz et al. ......... 128/DIG. 12 |
| 5,147,311 A | * | 9/1992 | Pickhard ..................... 604/131 |
| 5,300,031 A | | 4/1994 | Neer et al. |
| 5,383,858 A | | 1/1995 | Reilly et al. |
| 5,779,675 A | | 7/1998 | Reilly et al. |

FOREIGN PATENT DOCUMENTS

WO     WO 98/20920     5/1998

OTHER PUBLICATIONS

International Search Report for Counterpart PCT Application No. PCT/US99/27574.

* cited by examiner

Primary Examiner—Thor Campbell
(74) Attorney, Agent, or Firm—Gregory L. Bradley

(57) ABSTRACT

A syringe system (20) includes an elongated shell (30), a pressure member (80) slidable disposed within the elongated shell (30), and a collapsible cartridge (100). The Collapsible cartridge (100) is inserted within the elongated shell (30), and collapses as the pressure member (30) is advanced within the elongated body (30) to pressurize fluid within the collapsible cartridge (100). The collapsible cartridge (100) preferably further includes a passage (130) through which the fluid passes when pressurized by the pressure member (80).

33 Claims, 9 Drawing Sheets

SYRINGES AND INJECTOR SYSTEMS WITH COLLAPSIBLE CARTRIDGES

This application claims the benefit of Provisional application Ser. No. 60/109,476 filed Nov. 23, 1998.

FIELD OF THE INVENTION

The present invention relates to syringe systems and injector systems and, more particularly, to medical syringe systems and injector systems with collapsible cartridges for containing and pressurizing the injection fluid.

BACKGROUND OF THE INVENTION

Syringes have been used in the medical arts for many decades now. In general, all syringes include a barrel or chamber into which a fluid to be injected is charged. The syringes also include a reciprocating plunger that is advanced to pressurize the fluid within the barrel for injection and retracted to draw fluid into the barrel.

In recent years, a number of injector-actuated syringes and powered injectors for use in medical procedures such as angiography, computed tomography, ultrasound and MRI have been developed. For example, U.S. Pat. No. 4,006,736 discloses an apparatus for injecting fluid into the vascular system of a human being or an animal. Likewise, U.S. Pat. No. 4,677,980 discloses an angiographic injector and syringe wherein the drive member of the injector can be connected to, or disconnected from, the syringe plunger at any point along the travel path of the plunger via a releasable mechanism. Further, U.S. Pat. No. 5,383,858 discloses a non-pressure-jacketed front-loading syringe and injector system.

Although numerous advances have been made in syringe technology, numerous problems persist. For example, plungers used in current syringes typically comprise an elastomeric plunger cover that forms a sliding seal with the inside of the syringe barrel, usually requiring a lubricant to reduce frictional forces. Although maintenance of sterility is of the utmost importance in many medical procedures, lubricants used in connection with the plunger may come into contact with and contaminate the injection medium. Moreover, the inside wall of the syringe barrel may become contaminated during the reciprocating motion of the plunger.

In addition to maintaining sterility, it is also very important to inject a predetermined amount of material in many medical procedures. Often, if the wrong amount of injection medium is drawn into the syringe and injected, the procedure must be redone. In certain cases, disposable syringes are supplied in a "prefilled" state to assist in ensuring sterility and a controlled injection volume. However, current prefilled syringes are rather difficult to produce and require specialized materials.

It is very desirable to develop syringes that reduce or eliminate the problems discussed above and other problems associated with current syringes.

SUMMARY OF THE INVENTION

In one embodiment, the present invention provides a syringe system including an elongated shell, a pressure member slidably disposed within the elongated shell, and a collapsible cartridge. The collapsible cartridge is inserted within the elongated shell. The collapsible cartridge collapses as the pressure member is advanced within the elongated body to pressurize fluid within the collapsible cartridge. The collapsible cartridge preferably further includes a passage through which the fluid passes when pressurized by the pressure member.

The collapsible cartridge is preferably fabricated from a pliant or collapsible film suitable to withstand pressures commonly experienced in medical procedures such as angiography, computed tomography, ultrasound and MRI when the collapsible cartridge is pressurized within the shell. The shell preferably acts as a pressure jacket to assist in withstanding such pressures.

The pressure member of the syringe system may include an attachment mechanism to form an attachment with a drive member of a powered injector, as known in the art. For example, the attachment mechanism may be formed in the manner shown and described in U.S. Pat. Nos. 4,677,980 and 5,383,858. Alternately, however, in the event that the cartridge is prefilled with fluid, the pressure member may be designed to be "push-only," thereby not requiring an attachment mechanism to allow retraction of the pressure member for, for example, filling the cartridge with fluid.

The present invention also provides a method of injecting a fluid into a patient including the steps of: loading a collapsible cartridge for containing the fluid into an elongated shell, the collapsible cartridge comprising a passage through which the fluid passes when pressurized by a pressure member slidably disposed within the shell; and advancing the pressure member to collapse the collapsible cartridge and thereby pressurize the fluid within the collapsible cartridge.

The collapsible cartridges of the present invention may be prefilled with injection fluid before loading thereof into the shell of the syringe system or may be filled with injection fluid thereafter.

The syringe systems of the present invention are very simple and inexpensive to manufacture. For example, they greatly simplify and reduce the cost of manufacturing a disposable, prefilled syringe system that may be used with a single patient in a single injection procedure. The syringe systems of the present invention may be manually operated or injector-actuated, depending on the application. Moreover, the syringe systems of the present invention eliminate the need for a plunger that forms a seal with the inner wall of the syringe barrel. Contamination concerns arising from the use of elastomeric plunger covers and associated lubricants are thereby eliminated.

BRIEF DESCRIPTION OF THE DRAWINGS

Other aspects of the invention and their advantages will be discerned from the following detailed description when read in connection with the accompanying drawings, in which.

DETAILED DESCRIPTION OF THE INVENTION

Figure 1A:
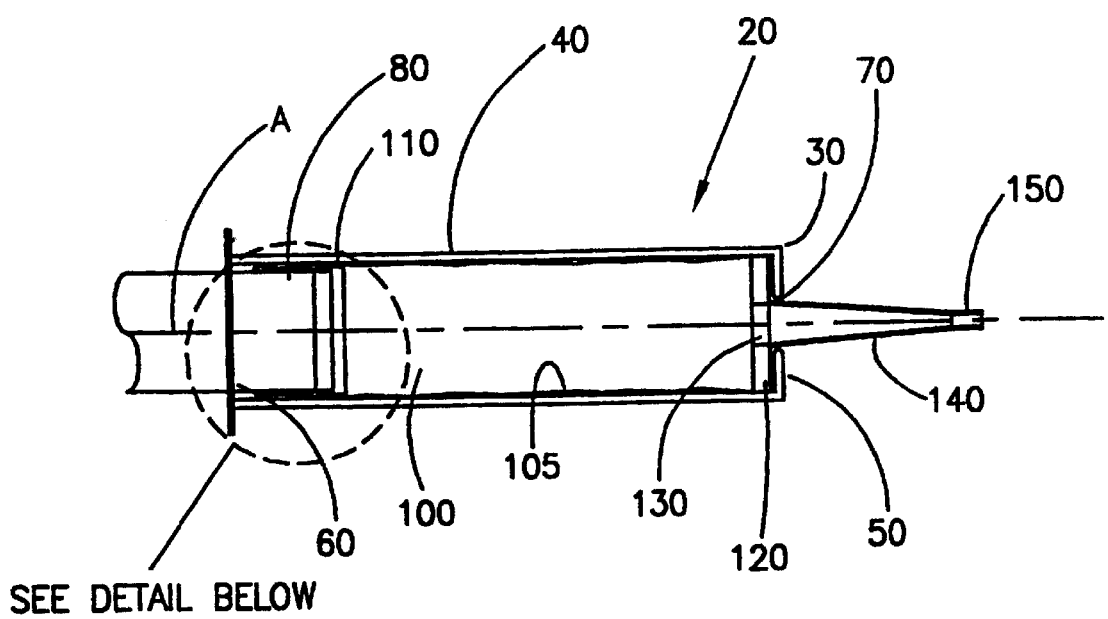
FIG. 1A illustrates a cross-sectional view of one embodiment of a syringe system of the present invention.
Figure 1A:
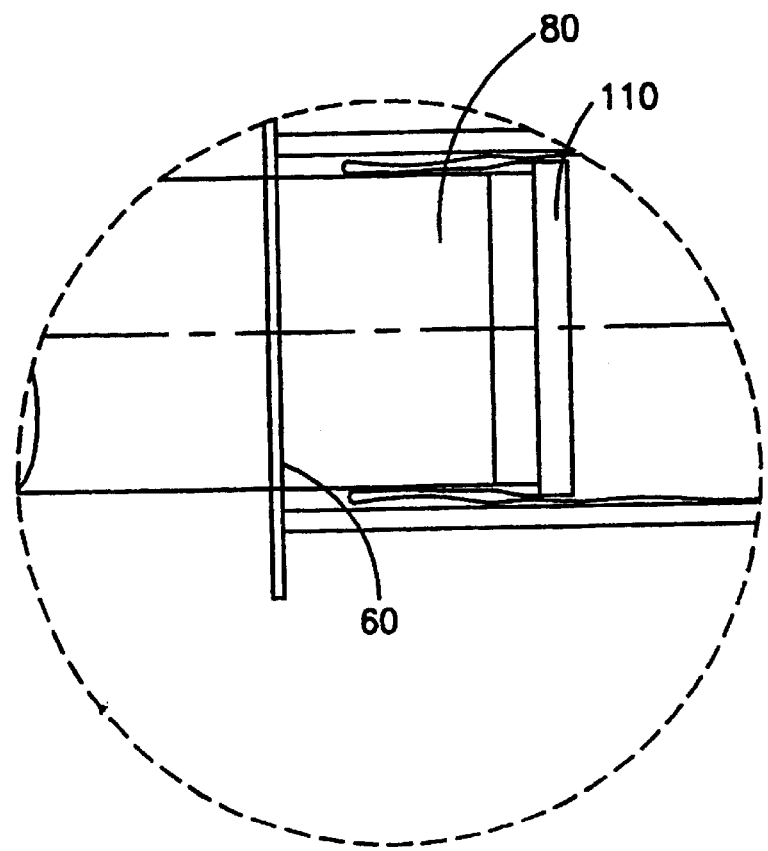
Figure 1B:
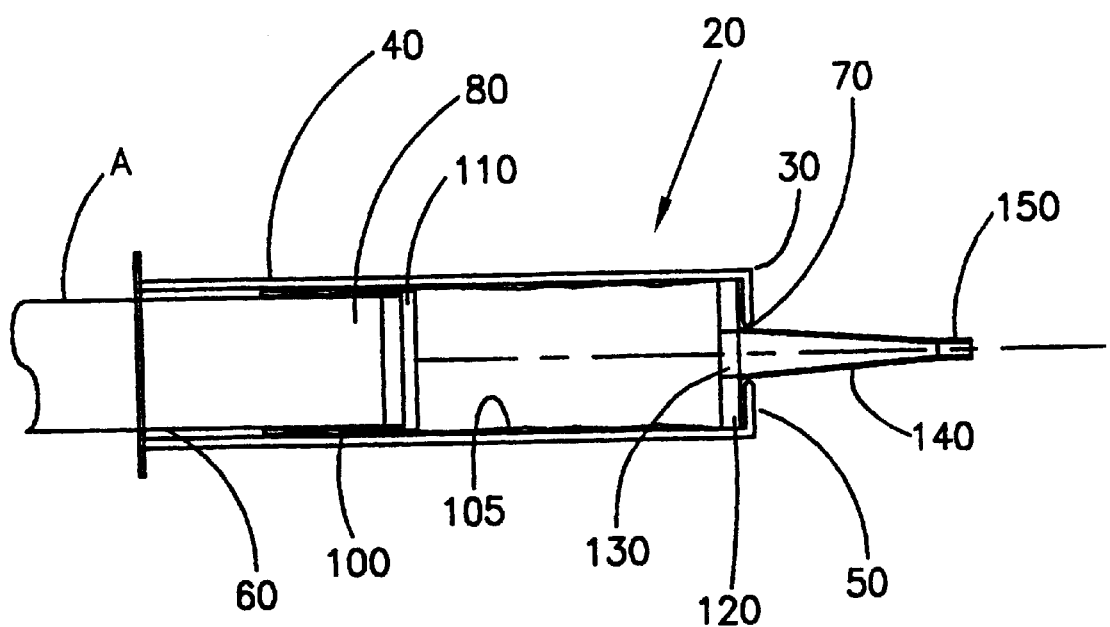
FIG. 1B illustrates a cross-sectional view of the syringe system of FIG. 1A in which the pressure member has been advanced.
Figure 1C:
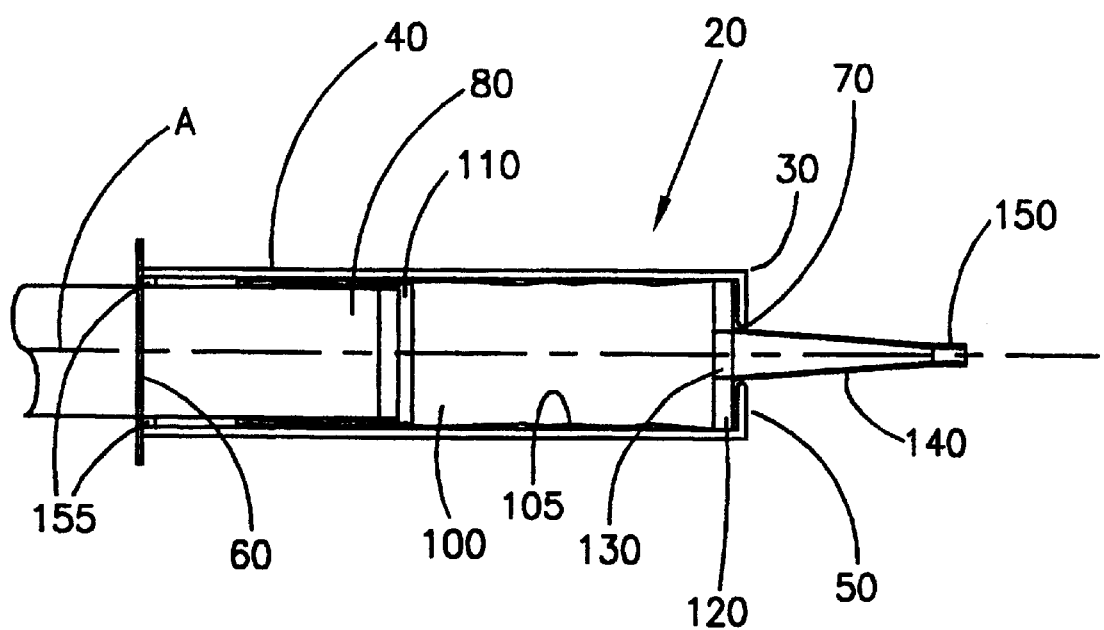
FIG. 1C illustrates a cross-sectional view of the syringe system of FIG. 1A in which a seal has been provided to prevent air from entering into the area between the pressure member and the barrel of the shell.

A first embodiment of a syringe system 20 of the present invention is illustrated in FIGS. 1A–1C. Syringe system 20 preferably includes a relatively rigid outer shell or jacket 30. Shell 30 preferably includes an elongated, generally cylindrical barrel portion 40. Shell 30 preferably further includes a forward abutment wall 50 at a forward end of barrel portion 40.

Figure 2A:
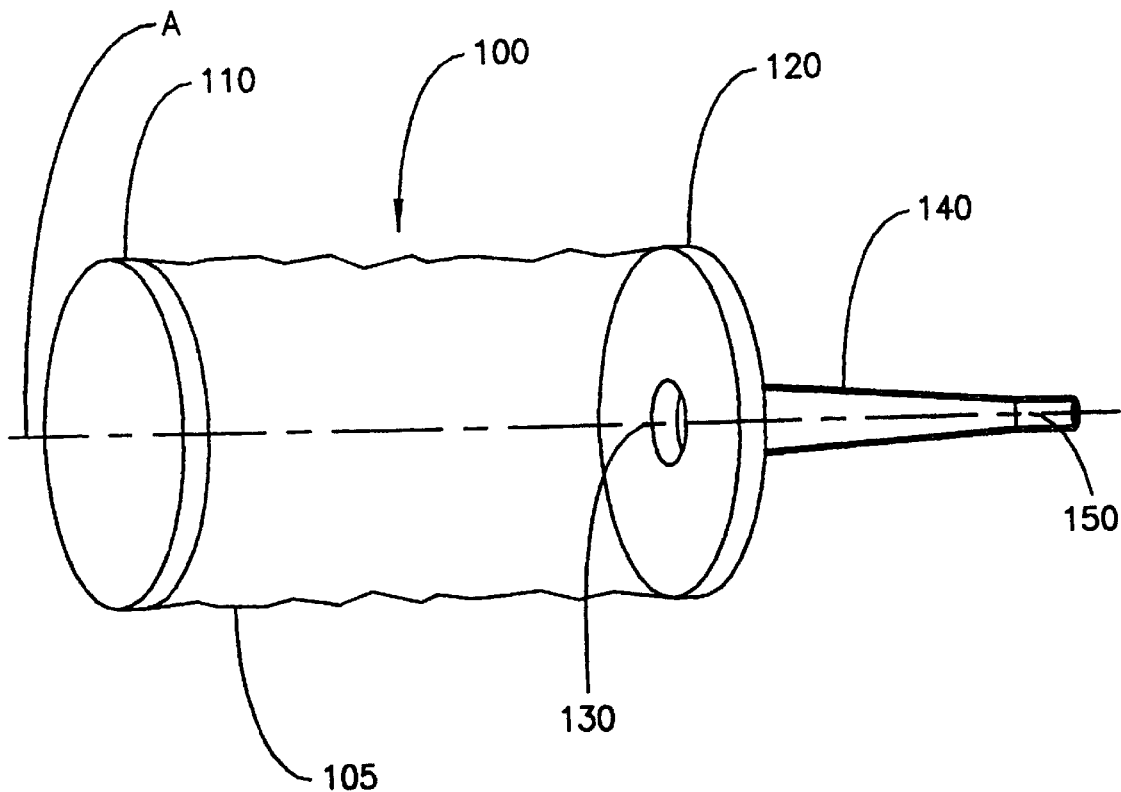
FIG. 2A illustrates a perspective view of the collapsible cartridge of the embodiment of FIG. 1.

Syringe system 20 also includes a collapsible cartridge 100 as further illustrated in FIG. 2A. Collapsible cartridge 100 preferably includes a generally cylindrical collapsible film 105, which may be formed from polyethylene (PET), polypropylene (PP) or polyurethane (PU).

At a rearward end of collapsible film 105, a first, relatively rigid end portion 110 may be sealingly attached to collapsible film 105. At a forward end of collapsible film 105, a second, relatively rigid end portion 120 may be sealingly attached to collapsible film 105. Collapsible film 105 and end portions 110 and 120 form a collapsible chamber into which a fluid to be injected into a patient can be charged.

Second end portion 120 preferably comprises a. passage 130 therethrough. Passage 130 is preferably in fluid connection with a tapered discharge or injection region 140. Pressurized injection fluid is discharged from a discharge tip 150. Tapered injection region 140 preferably extends through a forward, annular passage 70 formed in abutment wall 50.

Collapsible cartridge 100 is preferably loaded within barrel portion 30 from a rearward end 60 of barrel portion 30. Discharge tip 150 of collapsible cartridge 150 is preferably provided with a sealing cap member (not shown) to retain the injection fluid within collapsible cartridge 100 for shipment and storage of collapsible cartridge 100. Discharge tip 150 may for example comprise a luer connection for connection to tubing (after removal of the sealing cap member) as known in the art.

Syringe system 20 preferably further comprises a pressurizing member or pressure member 80 slidably disposed in barrel 40 of shell 30. Pressure member 80 is advanced forward to pressurize the fluid within collapsible cartridge 100.

Unlike the case of current syringes incorporating plungers, there is no requirement to form a seal between pressure member 80 and the inside wall of barrel portion 40 and, therefore, no sliding force on the inside wall of barrel portion 40. The use of lubricants is thus eliminated. Moreover, pressure member 80 never comes into contact with the fluid within collapsible cartridge 100 and need not even contact the inner wall of barrel portion 40, thereby greatly reducing the risk of fluid contamination. The fluid is pressurized by reducing the volume of collapsible cartridge 100 upon forward motion of pressure member 80.

In the embodiment of FIGS. 1A–1C, as pressure member 80 is advanced forward within barrel portion 40, collapsible film 105 preferably everts on itself. During such advancement of pressure member 80, collapsible film 105 is held rigidly against shell 30 and against pressure member 40 by pressure in the injection fluid. As pressure member 40 advances forward, collapsible film 105 moves from being in contact with shell 30 and everts to be in contact with pressure member 80.

Figure 2B:
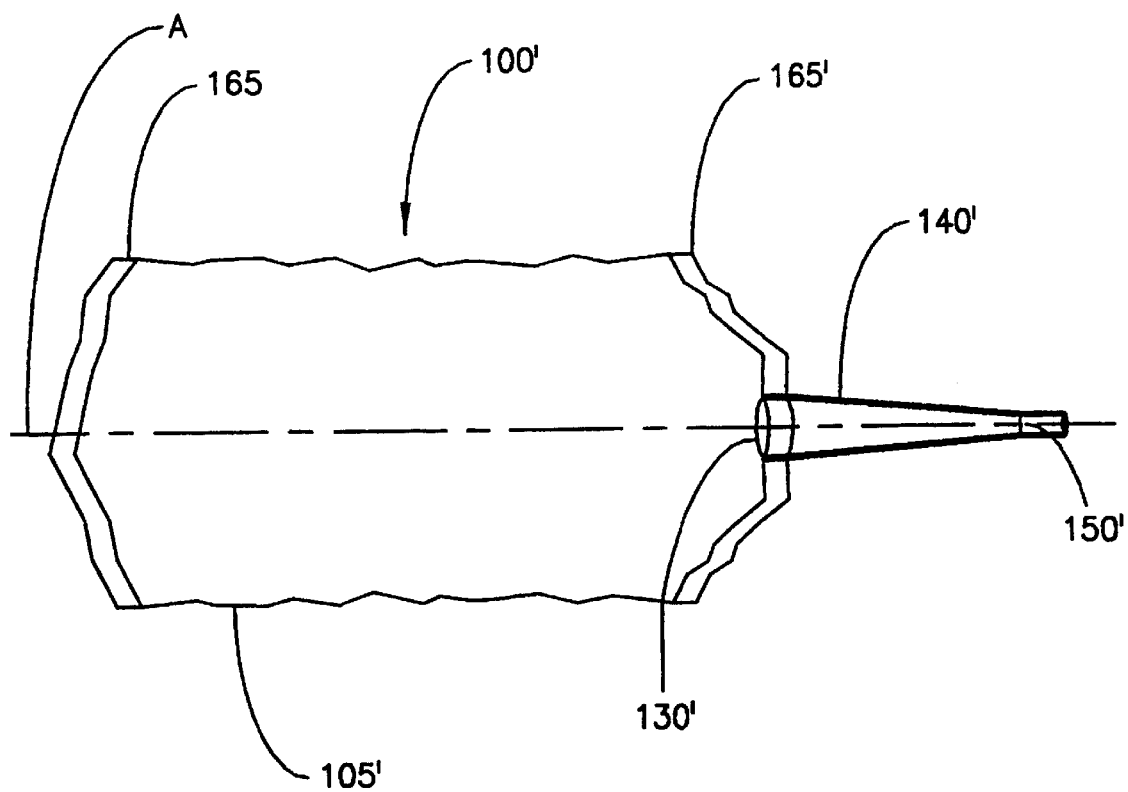
FIG. 2B illustrates a perspective view of another embodiment of a collapsible cartridge of the present invention.

Another embodiment of a collapsible cartridge 100' is illustrated in FIG. 2B. In this embodiment, collapsible cartridge 100' comprises a collapsible film 105' that is preferably sealed at the rearward end thereof with a seam or seal 165 and at a forward end thereof with seam or seal 165' of film 105'. Another seam or seal (not shown) may extend longitudinally or axially down the side of collapsible cartridge 100'. The interior of collapsible cartridge 100' is preferably in fluid connection with a tapered discharge or injection region 140' via a passage 130'. As described above, pressurized injection fluid is discharged from a discharge tip 150'.

As clear to one skilled in the art, prefilled, disposable, collapsible cartridges (as, for example, illustrated in FIGS. 2A and 2B) are easily inserted into shell 30. In some cases, however, it may be desirable to fill the collapsible cartridge with injection fluid after insertion thereof and, potentially, to reuse the collapsible cartridge for multiple injection procedures.

In the case of the syringe system 20 as illustrated in FIGS. 1A and 1B, however, collapsible cartridge 100 or 100' would be difficult to fill with injection fluid after insertion thereof in shell 30. In that regard, if pressure member 80 were attached to (or formed integrally with) rearward end 110 of collapsible cartridge 100 and drawn rearward, collapsible film 105 would collapse.

In the embodiment of FIG. 1C, a generally cylindrical seal 155 is positioned at the rearward end of shell 30 to provide a sealing engagement between pressure member 80 and shell 30. Because seal 155 prevents air from entering the space between pressure member 80 and barrel portion 40 of shell 30, when pressure member 80 is drawn rearward injection fluid can be drawn into collapsible cartridge 100 or 100'. Seal 155 can be very simple in design as it needs to sustain only approximately 1 atmosphere of pressure, in a preferred embodiment.

As used herein to describe syringe system 20 and collapsible cartridges 100 and 100', the terms "axial" or "axially" refer generally to an axis A around which syringe system 20 and collapsible cartridge 100 are preferably formed (although not necessarily symmetrically therearound) The terms "proximal" or "rearward" refer generally to an axial direction toward the end of syringe system 20 opposite discharge tip 150 or 150'. The terms "distal" or "forward" refer generally to an axial direction toward discharge tip 150 or 150' of syringe system 20. The term "radial" refers generally to a direction normal to axis A.

Preferably, the syringe systems of the present invention are used in connection with a powered injector 310 (see FIG. 3A) as known in the art. Powered injectors suitable for use in the present invention are disclosed in U.S. Pat. Nos. 4,677,980, 5,383,858, 5,779,675 and 5,300,031, the disclosures of which are incorporated herein by reference. Alternately, however, the syringe systems of the present invention can be readily applied to hand-held or manually-operated syringes.

Figure 3A:
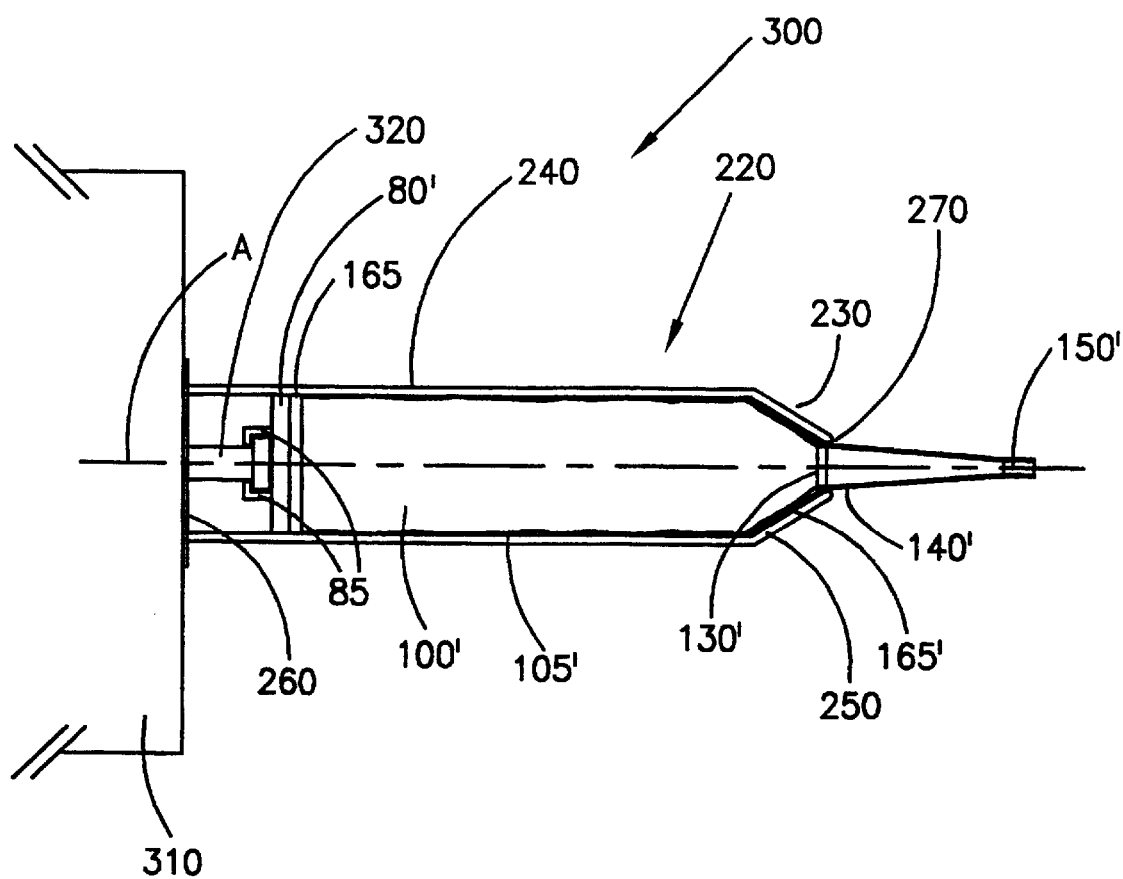
FIG. 3A illustrates a cross-sectional view of another embodiment of a syringe system and an injector system of the present invention.
Figure 3B:
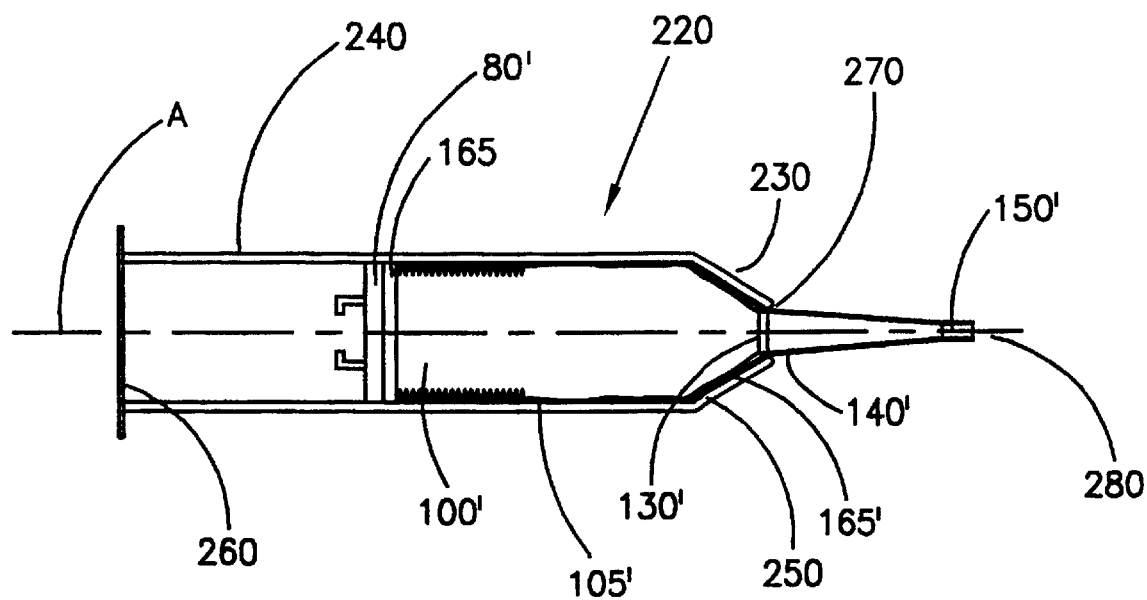
FIG. 3B illustrates a cross-sectional view of the syringe system of FIG. 3A in which the pressure member has been advanced.

Syringe molds/designs and injector systems currently in use are relatively easily retrofitted for use with the collapsible cartridges of the present invention. In that regard, such syringes can act as the shell or jacket for the collapsible cartridges of the present invention with only minor modification. In FIGS. 3A and 3B, for example, an injector system 300 and a syringe system 220 are illustrated. Syringe system 220 comprises a shell 230 that is very similar to many syringes currently in use with front-loading powered injectors, such as the injector and syringe system shown and described in U.S. Pat. No. 5,383,858, the contents of which are hereby incorporated by reference.

As known in the art, shell/syringe 220 preferably comprises an elongated, generally cylindrical body or barrel section 240. A generally frusto-conical transition region 250 is preferably positioned at the forward end of cylindrical body 240. Collapsible cartridge 100' is illustrated within the interior of shell 230 as loaded through rearward shell end 260. Tapered injection region 140' extends through a passage 270 formed at the forward end of frusto-conical transition region 250.

Figure 3C:
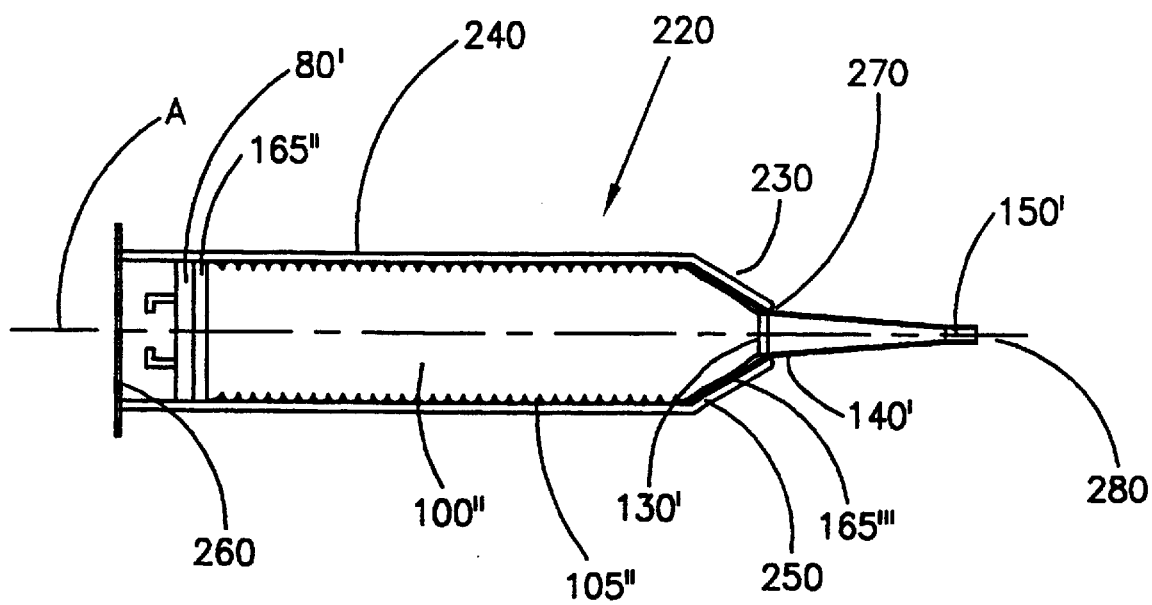
FIG. 3C illustrates a cross-sectional view of another embodiment of a syringe system of the present invention having a collapsible cartridge that is preformed or pre-stressed to collapse in a controlled manner.
Figure 4:
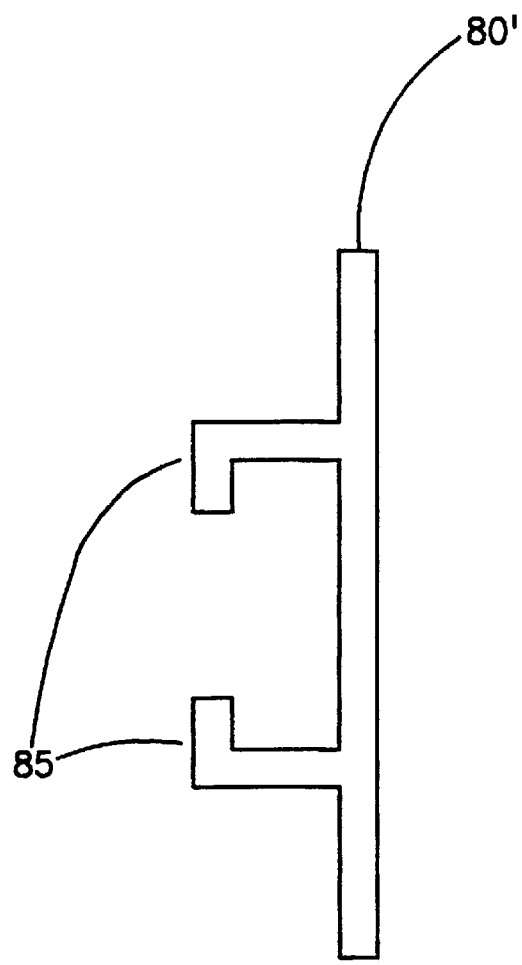
FIG. 4 illustrates a side view of a pressure member for use with the collapsible cartridges of the present invention.

As illustrated in FIGS. 3A through 4, pressure member 80' may comprise capture member 85 to preferably form a releasable connection with a piston member 320 of a powered injector 310, as known in the art from U.S. Pat. Nos. 4,677,980 and 5,383,858 and PCT Publication No. WO 98/20920, the contents of which are hereby incorporated by reference.

In the embodiment of FIGS. 3A and 3B, the space between pressure member 80' and the inner wall of barrel member 240 is too small to allow the everting movement of collapsible film 105' as discussed in connection with the embodiments of FIGS. 1A through 1C. In the embodiment of FIGS. 3A and 3B, collapsible film 105' collects at the rear of collapsible cartridge 100' as pressure member 80' is advanced and pressurized injection fluid is discharged from discharge tip 150'. Once again, however, there is no need for the formation of a sealing engagement (or even contact) between pressure member 80' and the inner wall of barrel portion 240 to pressurize the fluid within collapsible cartridge 100'. Pressure member 80 can, however, form a seal with barrel portion 40 adequate to sustain approximately 1 atmosphere of pressure to enable filling of collapsible cartridge 100' upon retraction of pressure member 801.

For applications in which injection volume need not be precisely controlled, collapsible film 105' can be allowed to collect at the rearward end thereof in an uncontrolled "scrunch" as illustrated in FIG. 3B. In cases in which it is desirable to more accurately control the volume of fluid injected, the collapsible film can be preformed or prestressed to give some order to the scrunch. In FIG. 3C, for example, collapsible film 105" has been preformed in the shape of a bellows to provide an orderly collapse thereof upon advance of pressure member 80'.

It should be appreciated that the syringe systems of the present invention may be configured in various ways and as appropriate for the application. The embodiments described above are to be considered in all respects as being illustrative of the invention, and not restrictive. The scope of the invention is indicated by the following claims rather than by the foregoing description. All changes which fall within the meaning and range of equivalency of the claims are to be embraced within their scope.

What is claimed is:

1. A syringe system comprising:
   a shell;
   a pressure member slidably disposed within the shell;
   a collapsible cartridge adapted to be inserted within the shell, the collapsible cartridge operable to collapse as the pressure member is advanced within the shell to pressurize fluid contained within the collapsible cartridge, the collapsible cartridge comprising a passage through which the fluid passes when pressurized by the pressure member; and
   a seal disposed between the pressure member and the shell, the seal operable to allow the cartridge to be filled with fluid when the pressure member is retracted to draw fluid into the collapsible cartridge.

2. The syringe system of claim 1 wherein the pressure member comprises an attachment mechanism.

3. The syringe system of claim 2 wherein the attachment mechanism is operable to form an attachment with a drive member of a powered injector.

4. The syringe system of claim 1 wherein the seal is generally cylindrical.

5. The syringe system of claim 1 wherein the seal is positioned at a rearward end of the shell.

6. The syringe system of claim 1 wherein the collapsible cartridge comprises a pliant film suitable to withstand pressures commonly experienced in medical procedures while pressurized within the shell.

7. The syringe system of claim 1 wherein the collapsible cartridge is filled with the fluid prior to insertion of the collapsible cartridge within the shell.

8. The syringe system of claim 1 wherein the pressure member is adapted to be manually-actuated.

9. The syringe system of claim 1 wherein the collapsible cartridge comprises a bellows to allow the cartridge to collapse in an orderly fashion.

10. The syringe system of claim 1 wherein the collapsible cartridge is adapted to evert upon itself within the shell.

11. A cartridge for use in a shell, the cartridge comprising:
    a pressure member slidably disposed within the shell;
    a collapsible member adapted to be inserted within the shell, the collapsible member operable to collapse as the pressure member is advanced within the shell to pressurize fluid contained within the collapsible member, the collapsible member comprising a passage through which the fluid passes when pressurized by the pressure member; and
    a seal disposed between the pressure member and the shell, the seal operable to allow the collapsible member to be filled with fluid when the pressure member is retracted to draw fluid into the collapsible member.

12. The cartridge of claim 11 wherein the pressure member comprises an attachment mechanism.

13. The cartridge of claim 12 wherein the attachment mechanism is operable to form an attachment with a drive member of a powered injector.

14. The cartridge of claim 11 wherein the seal is generally cylindrical.

15. The cartridge of claim 11 wherein the seal is positioned at a rearward end of the shell.

16. The cartridge of claim 11 wherein the collapsible member comprises a pliant film suitable to withstand pressures commonly experienced in medical procedures while pressurized within the shell.

17. The cartridge of claim 11 wherein the collapsible member is filled with the fluid prior to insertion of the collapsible member within the shell.

18. The cartridge of claim 11 wherein the pressure member is adapted to be manually-actuated.

19. The cartridge of claim 11 wherein the collapsible member comprises a bellows to allow the member to collapse in an orderly fashion.

20. The cartridge of claim 11 wherein the collapsible member is adapted to evert upon itself within the shell.

21. A method of injecting a fluid into a patient, the method comprising:

provinding a collapsible cartridge for insertion into a shell, the collapsible cartridge comprising a passage through which the fluid passes from the collapsible cartridge to the patient;

providing a pressure member for pressurizing the fluid placed within the collapsible cartridge for injection into the patient;

providing a seal disposed between the pressure member and the shell, the seal operable to allow the cartridge to be filled with fluid when the pressure member is retracted to draw fluid into the collapsible cartridge;

inserting the collapsible cartridge into the shell; and advancing the pressure member to collapse the collapsible cartridge and thereby pressurize the fluid within the collapsible cartridge for injection into the patient.

22. The method of claim 21, further comprising retracting the pressure member to fill the collapsible cartridge with fluid.

23. The method of claim 21, further comprising:

removing the collapsed cartridge from the shell; and inserting a second collapsible cartridge into the shell.

24. The method of claim 21 wherein the pressure member is manually advanced.

25. A fluid injection apparatus comprising:

a housing;

a drive member disposed within the housing; and a syringe system operably associated with the housing and the drive member, the syringe system comprising a shell operably associated with the housing, a pressure member operable to be engaged by the drive member and slidably disposed within the shell, a collapsible cartridge adapted to be inserted within the shell and operable to be engaged by the pressure member, the collapsible cartridge operable to collapse as the pressure member is advanced by the drive member within the shell to pressurize fluid within the collapsible cartridge, the collapsible cartridge comprising a passage through which the fluid passes when pressurized by the pressure member, and a seal disposed between the pressure member and the shell, the seal operable to allow the cartridge to be filled with fluid when the pressure member is retracted to draw fluid into the collapsible cartridge.

26. The fluid injection apparatus of claim 25 wherein the pressure member and the drive member comprise mating elements of an attachment mechanism.

27. The fluid injection apparatus of claim 26 wherein the attachment mechanism allows the drive member to retract the pressure member within the shell.

28. The fluid injection apparatus of claim 25 wherein the seal is positioned at a rearward end of the shell.

29. The fluid injection apparatus of claim 25 wherein the collapsible cartridge comprises a pliant film suitable to withstand pressures commonly experienced in medical procedures while pressurized within the shell.

30. The fluid injection apparatus of claim 25 wherein the collapsible cartridge is filled with the fluid prior to insertion of the collapsible cartridge within the shell.

31. The fluid injection apparatus of claim 25 wherein the pressure member is adapted to be manually-actuated.

32. The fluid injection apparatus of claim 25 wherein the collapsible cartridge comprises a bellows to allow the cartridge to collapse in an orderly fashion.

33. The fluid injection apparatus of claim 25 wherein the collapsible cartridge is adapted to evert upon itself within the shell.

* * * * *